(12) United States Patent
Apblett et al.

(10) Patent No.: US 8,647,451 B2
(45) Date of Patent: Feb. 11, 2014

(54) NANOMETRIC INK FOR DETECTION OF EXPLOSIVES

(75) Inventors: Allen Wallace Apblett, Stillwater, OK (US); Nicholas Ferdinand Materer, Stillwater, OK (US)

(73) Assignee: The Board of Regents for Oklahoma State University, Stillwater, OK (US)

(*) Notice: Subject to any disclaimer, the term of this patent is extended or adjusted under 35 U.S.C. 154(b) by 584 days.

(21) Appl. No.: 12/825,846

(22) Filed: Jun. 29, 2010

(65) Prior Publication Data
US 2012/0156795 A1    Jun. 21, 2012

Related U.S. Application Data

(60) Provisional application No. 61/221,283, filed on Jun. 29, 2009.

(51) Int. Cl.
*C06B 45/00* (2006.01)
*D03D 23/00* (2006.01)
*D03D 43/00* (2006.01)

(52) U.S. Cl.
USPC ....... 149/2; 149/108.8; 149/109.4; 149/109.6

(58) Field of Classification Search
USPC .............................. 149/2, 108.8, 109.4, 109.6
See application file for complete search history.

(56) References Cited

U.S. PATENT DOCUMENTS

| | | | |
|---|---|---|---|
| 3,880,588 A * | 4/1975 | Rittersdorf et al. | 436/97 |
| 4,753,916 A * | 6/1988 | Carcia et al. | 502/321 |
| 5,123,274 A * | 6/1992 | Carroll et al. | 73/863.12 |
| 5,480,612 A | 1/1996 | Margalit | |
| 5,648,047 A | 7/1997 | Kardish et al. | |
| 6,767,717 B1 | 7/2004 | Itzhaky et al. | |
| 6,819,811 B1 * | 11/2004 | Goldstein | 385/12 |
| 7,294,306 B2 | 11/2007 | Haas et al. | |
| 7,390,674 B2 | 6/2008 | Feaster et al. | |
| 2006/0079410 A1 * | 4/2006 | Yadav | 508/165 |
| 2006/0145091 A1 | 7/2006 | Patel | |
| 2007/0202009 A1 | 8/2007 | Nunes et al. | |
| 2008/0182334 A1 | 7/2008 | Amisar | |
| 2009/0029480 A1 | 1/2009 | Loane | |
| 2009/0068065 A1 | 3/2009 | Pagoria et al. | |
| 2009/0275143 A1 | 11/2009 | Misra et al. | |

FOREIGN PATENT DOCUMENTS

WO    PCT/US10/040412    3/2011

OTHER PUBLICATIONS

Bussan (Applications of Molybdenum Utilized in Sensing Devices, 2004).*
Burks, Raychelle et al., "Current trends in the detection of peroxide-based explosives", Anal Bioanal Chem, 2009, pp. 301-313, vol. 395.
Materer, Nicholas et al., "The Preparation and Chemical Reaction Kinetics of Microcrystalline Tungsten Bronze Thin Flims with Nitrobenzene and Iron (III) Solutions" (Abstract Only), http://acs.confex.com/acs/swrm08/techprogram/P62126.HTM, Oct. 2, 2008.

(Continued)

*Primary Examiner* — James McDonough
(74) *Attorney, Agent, or Firm* — Fellers, Snider, Blankenship, Bailey, & Tippens, P.C.; Terry L. Watt

(57) ABSTRACT

A method of manufacturing an explosive testing agent is disclosed. The method includes synthesizing hydrogen bronze nanoparticles and placing the nanoparticles on a test platform.

5 Claims, 2 Drawing Sheets

(56) References Cited

OTHER PUBLICATIONS

Apblett et al., "Nanotechnology for neutralization of terrorist explosives (Abstract Only)", "Ceramic Transactions", 2005, pp. 29-35, vol. 172, Publisher: American Ceramic Society, Published in: Westerville, OH.

Moore, David S., "Recent Advances in Trace Explosives Detection Instrumentation", "Sens Imaging", May 26, 2007, pp. 9-38, vol. 8, Publisher: Springer Science+Business Media, LLC.

Singh, "Sensors—An effective approcah for the detection of explosives", "Journal of Hazardous Materials", Feb. 7, 2007, pp. 15-28, vol. 144, Publisher: Elsevier.

Apblett, Allen W. et al., "Nanotechnology for Neutralization of Terrorist Explosives", 2005, pp. 29-35, vol. 172, Publisher: American Ceramic Society, Published in: US.

\* cited by examiner

NANOMETRIC INK FOR DETECTION OF EXPLOSIVES

CROSS REFERENCE TO RELATED APPLICATIONS

This application claims the priority of U.S. Provisional Patent Application No. 61/221,283 entitled "NANOMETRIC INK FOR DETECTION OF EXPLOSIVES," filed Jun. 29, 2009, the contents of which are hereby incorporated by reference.

STATEMENT REGARDING FEDERALLY SPONSORED RESEARCH OR DEVELOPMENT

This invention was made with government support under grant number ECCS-0731208 awarded by the National Science Foundation. The government has certain rights in the invention.

BACKGROUND OF THE INVENTION

Explosives pose a deadly risk to our society as a consequence of intentional use by terrorists and accidental detonation resulting from mishandling of explosives, discharge of unexploded ordinance, or even build up of peroxides in otherwise safe solvents. While there are a large number of sensor technologies for explosives, there is a significant shortfall in ones that can detect improvised explosives such as peroxide-based explosives. There is an even larger dearth of technologies that can be used for detecting both nitro-organic explosives and peroxide explosives.

What is needed is a system and method for addressing the above and related issues.

SUMMARY OF THE INVENTION

The present invention disclosed and claimed herein, in one aspect thereof, comprises a method of manufacturing an explosive testing agent. The method includes synthesizing hydrogen bronze nanoparticles, and placing the nanoparticles on a test platform. Synthesizing hydrogen bronze nanoparticles may further comprise exposing molybdenum trioxide to an acid salt. Synthesizing hydrogen bronze nanoparticles could also comprise exposing tungsten trioxide to an acid salt. The acid salt may be a salt of a 2-hydroxycarboxylic acid. The 2-hydroxycarboxylic acid may be sodium gluconate.

In another aspect thereof, the invention disclosed and claimed herein comprises a kit for testing for the presence of explosive. The kit includes a test platform provided with hydrogen bronze nano particles along with a carrier allowing a test subject to come in contact with the nano particles, the carrier allowing the observation of color changes of the nano particles.

DETAILED DESCRIPTION OF THE PREFERRED EMBODIMENTS

Figure 1:
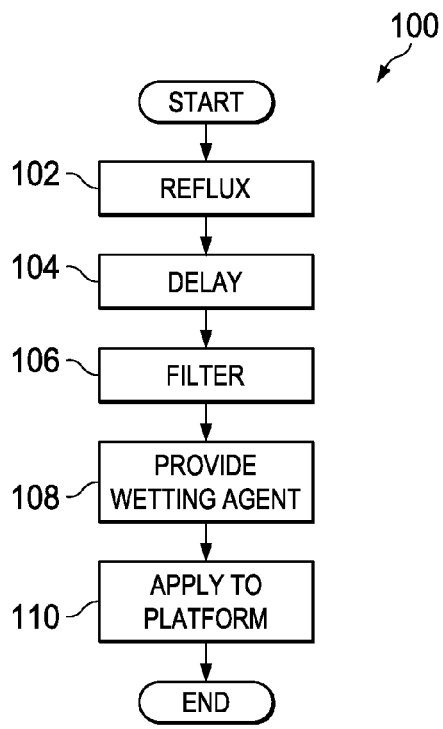
FIG. 1 is a flow chart illustrating a method of producing a nanometric ink based explosives test platform according to the present disclosure.

A peroxide explosive is an organic compound that contains one or more peroxide functional groups (R—O—O—R), often in a cyclic form. Peroxides can display an explosive power that is on a par with high explosives. Peroxide explosives are usually unstable and are highly sensitive to heat, friction, shock, and impact, often making the use of an initiator redundant. Several peroxide explosives are known, such as hexamethylene-triperoxidediamine (HMTD), triacetonetriperoxide (TATP), diacetondiperoxide (DADP) and tetramethylenediperoxide carbamide (TMDD).

The danger of peroxide explosives is compounded by the fact that most of the ingredients for their manufacture can be obtained easily from local pharmacies and hardware stores. For example, explosives can readily be prepared using hydrogen peroxide and a few other common chemicals, such as acetone for TATP and DADP, hexamine (or ammonia and formaldehyde) for HMTD, and formaldehyde and urea for TMDD. A small amount of acid (such as hydrochloric, sulfuric, or citric acid) is used as a catalyst. Even more alarming, many recipes for the synthesis of these explosives can be obtained on the Internet.

The availability and difficulty of government control of the ingredients and the ease of synthesis of peroxide-based explosives have led to their extensive use by terrorist organizations. TATP, the most commonly used improvised explosive substance, has been blamed for a number of accidental explosions and has been used in several terrorist attacks in the USA, Israel and elsewhere in the world. Examples of recent terrorist use of TATP include the attacks on May 16, 2003, in Casablanca, Morocco and the so-called shoe bomber.

This disclosure describes reagents that can neutralize both peroxide-based improvised explosives and military explosives (such as RDX and TNT) under ambient conditions in a reaction that results in a remarkable change in color. These reagents are based on molybdenum or tungsten trioxide and are referred to as hydrogen bronzes. These compounds store hydrogen in the form of hydroxyl groups attached to reduced metal ions and are a stable, effective hydrogen storage compound. In this form, the hydrogen is completely non-flammable but still capable of behaving as a reducing reagent. These compounds are derived from reduction of molybdenum or tungsten trioxide with hydrogen or a hydrogen source such as an alcohol. They are highly colored compounds that contain pentavalent metal centers with attached hydroxides. The latter species have the unusual property of reacting as if they are hydridic rather than protic like a normal hydroxide. This is a result of the fact that transfer of the hydrogen ion to a substrate is usually accompanied by electron transfer and reification of the metal ion to the hexavalent state.

In some respects, the bronze can be considered to be a convenient storage medium for reactive hydrogen. For this reason the hydrogen bronzes are also useful for reduction of dangerous organic compounds such as peroxides, especially those that are used to create improvised explosives. These reagents work by reducing (Reaction I) the peroxide groups in the explosive to alcohol groups. This reduction occurs rapidly at room temperature. When contacted by TATP vapor present over solid TATP, an even more rapid response is visually observed. Molybdenum and tungsten hydrogen bronzes selectively reduce peroxide and nitro groups through a combined electron and proton transfer and are not sensitive to acetone, ketones, or other common organic species.

$$2Mo_2O_5(OH)+ROOH \rightarrow 4MoO_3+ROH+H_2O \qquad (1)$$

A brilliant blue suspension of molybdenum hydrogen bronze nanoparticles was originally synthesized by a reaction of molybdenum trioxide with butanol. For peroxide based explosives, these brilliant blue nanoparticles turn to a light yellow color as they react. Unfortunately, the use of organic solvents, particularly one that is somewhat toxic and has an objectionable smell is undesirable for commercial preparation of test strips and other sensors. Therefore, a water-based suspension of nanoparticles is also disclosed. We have demonstrated that molybdenum trioxide and tungsten trioxide react with metal salts of 2-hydroxycarboxylic acids to yield anionic complexes of the Group VI metals that serve as single source precursors for the corresponding metal molybdates. We have found that when this reaction is performed with an excess of the trioxide, nanoparticles in the range of 5-60 nm are prepared as stable, dark blue aqueous suspensions.

While a large range of carboxylic acids or their salts may be used for this purpose, the current embodiment uses sodium gluconate. In one example, sodium gluconate was refluxed in water with two molar equivalents of molybdenum trioxide. After 24 hours, a dark blue suspension was obtained which was separated by filtration from the solid hydrogen bronze by-product. The resulting aqueous suspension was determined to have a concentration of $HMO_2O_6$ of 6.2% by weight. The solution constitutes an "ink" that can be applied directly to suspected explosive compounds. This constitutes a major improvement over other detection systems.

The testing of liquid explosives, or for the vapors of explosives, may be conveniently done with test strips. Applying a liquid reagent, as described above, to a commercially available blank test strip produces a colored pad that is responsive to hydrogen peroxide vapor or liquid.

In some cases, the density of color on the pad may be uneven due to diffusion of the nanoparticles during drying. This problem is solved by adding 5% by weight of a water-soluble polymer (polyvinyl alcohol, PVA) to the aqueous solution.

In another example, an ink was prepared by refluxing a mixture of 1.0 g PVA, 2.19 g of sodium gluconate, and 2.9 g of $MoO_3$ in 20 ml of water for 18 hours. This gave a greenish blue ink with a concentration of $HMo_2O_6$ of 9.4% by weight. In one embodiment, a wetting agent may be added the ink to allow even wetting of the test strip pad.

Referring now to FIG. 1, a flow chart depicting an exemplary method of formulating the nanometric inks of the present disclosure, and adapting them into a test platform is shown. At step 102, the molybdenum trioxide (or tungsten trioxide) is refluxed with the appropriate acid salt in water. At step 104, a delay occurs to allow the reaction to take place which will produce the nano particulate. At step 106, the mixture is filtered to remove solids. At step 108, a wetting agent may be provided that may be needed to properly apply the mixture to the testing platform at step 110. In the case where the testing platform is to be a bottle or container (rather than a test strip, for example), the wetting agent may not be needed.

It will be appreciated that for purposes of the present disclosure, a testing platform may be any convenient way to deliver the ink to the presence of a potential explosive where a color change of the test ink may be observed. A non limiting example includes application of the ink to a commercially available test strip for observation of potential color change. The test strip may be placed inside a plastic bag with a sample of the test subject to make sure that any vapors emanating therefrom come in contact with the test strip. In another embodiment, the ink may be placed in an aerosol can and sprayed onto the suspected explosive. A pump spray bottle or dropper bottle may also be used. In one embodiment, the ink could be applied to a swab or patch and rubbed onto the suspected explosive or explosive container. The test subject could also be drawn into a capillary tube containing the ink.

In disclosed embodiments, "inks" based on suspensions of nanoparticles of molybdenum hydrogen bronze, $H_2Mo_3O_9$, may be commercialized for applications in detection of improvised explosives and prevention of peroxide formation in organic solvents. These dark blue suspensions turn colorless or pale yellow when they come in contact with explosives that contain peroxides, chlorates, or organic nitro groups.

Figure 2:
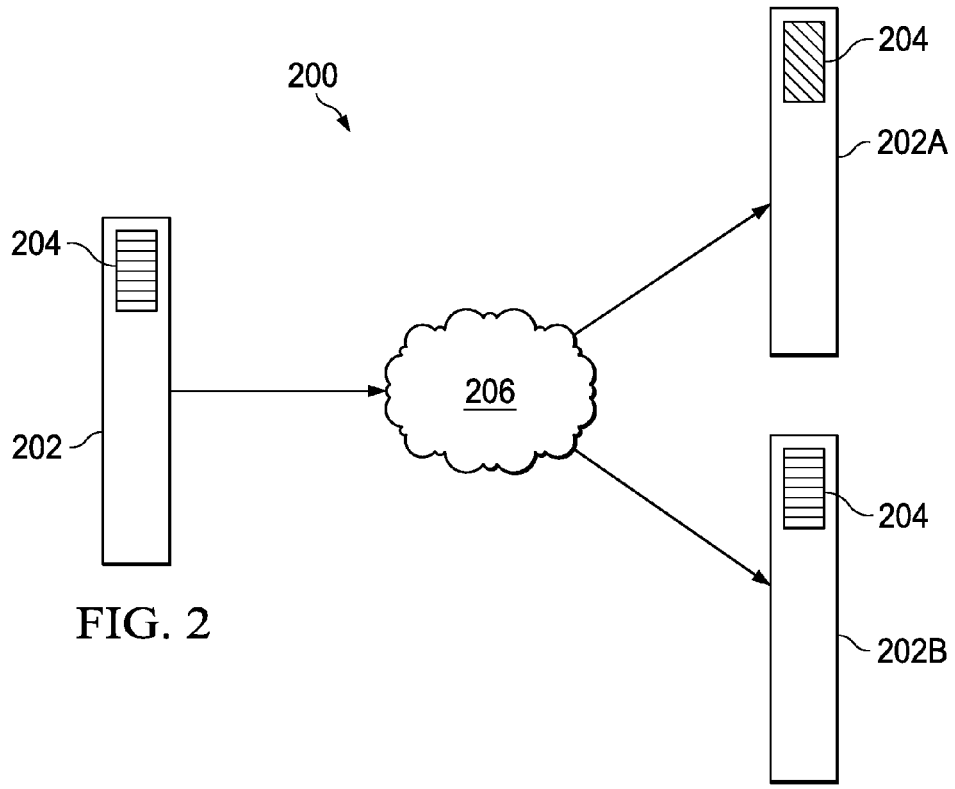
FIG. 2 is a plan diagram illustrating a method of testing for explosives using nanometric inks according to the present disclosure.

Referring now to FIG. 2, one embodiment of a testing process 200 utilizing a test strip prepared as described above is shown. The test strip 202 contains a surface 204 that has been treated with the nanometric testing ink. The test strip is exposed to the suspected explosive 206. This may be a container, an unknown substance, or vapors from the container or substance. If testing for vapors, the test strip and test subject may be placed in a sealed or semi sealed container (such as a plastic bag or other container). After exposure to the test subject, the test strip 202, shown now as 202A, may indicate a color change on the test surface 204. As described above, this change may be from a dark blue or green color to a pale yellow or other pale color. This would indicate the presence of an explosive. On the other hand, if the test strip 202, shown post testing as 202B, shows no change on the test surface 204, then an explosive has not been detected.

The test strips and the other test platforms described above represent some of the products that may be manufactured and commercialized. Namely, a test kit may be assembled that can identify whether or not a suspicious solid is an improvised explosive. This is of grave importance to security personnel or first responders confronted by such a material since the sensitivity of an improvised explosive material makes it extremely hazardous to move. There are only two main products currently servicing this market and both require sequential addition of two or more reagents making the present invention significantly more attractive and highly competitive. Furthermore, since the disclosed ink product is a single reagent, it can also be produced in a form of an aerosol that can be sprayed gently onto a suspected explosive. In the various embodiments, both drop-wise and spray-type test kits for peroxide and chlorate-based explosives may be manufactured.

While most explosives are solids, several liquid explosives do exist. There have also been attempts to smuggle the ingredients to manufacture explosives onto an airplane. These liquid explosives or liquid explosive ingredients can best be detected using test strips (described above) that may be produced by placing a spot of the ink of the present invention onto a plastic strip. We have shown these test strips to be successful in detecting peroxide-based explosives in liquid solutions or in the vapor phase. Currently, there are several types of enzyme-based test strips available, but all are very poor at detecting polyperoxides, such as those used in terrorist explosives. The nanometric inks allow the creation of test strips that can be stored at ambient temperature, have longer shelf life, and react instantaneously with hydrogen peroxide, peroxide-based improvised explosives, and chlorate-based explosives. The ease of use and stability of the inks clearly separate the product from the competition. Since these test strips respond to peroxide vapors, they could also be employed in the plastic bag currently required for a traveler's liquids and gel-based products. Some commercial detection companies have demonstrated that there is sufficient leakage from these bottles to provide vapors detectable by their expensive instrument. The change of a test strip's color is a much less expensive approach that could be more broadly applied, providing the color so inspection will require a brief glance at the package.

The ink can also be placed as a spot on the inside of a capillary tube for the purpose of aseptically testing of liquids meant for human or animal consumption. Such a liquid will be drawn up the tube by capillary action and when it contacts the ink spot, a color change will indicate the presence of an explosive or hydrogen peroxide that could be used to synthesize an improvised explosive. Other products designed for this purpose require the sequential addition of several reagents including very strong acids. They also cannot be produced as aerosol spray.

The inks can also be added drop-wise or as a spray to suspected explosives so that a color change will confirm the presence of improvised explosives. This method of detection is particularly useful for chlorate and peroxide-based explosives.

Figure 3:
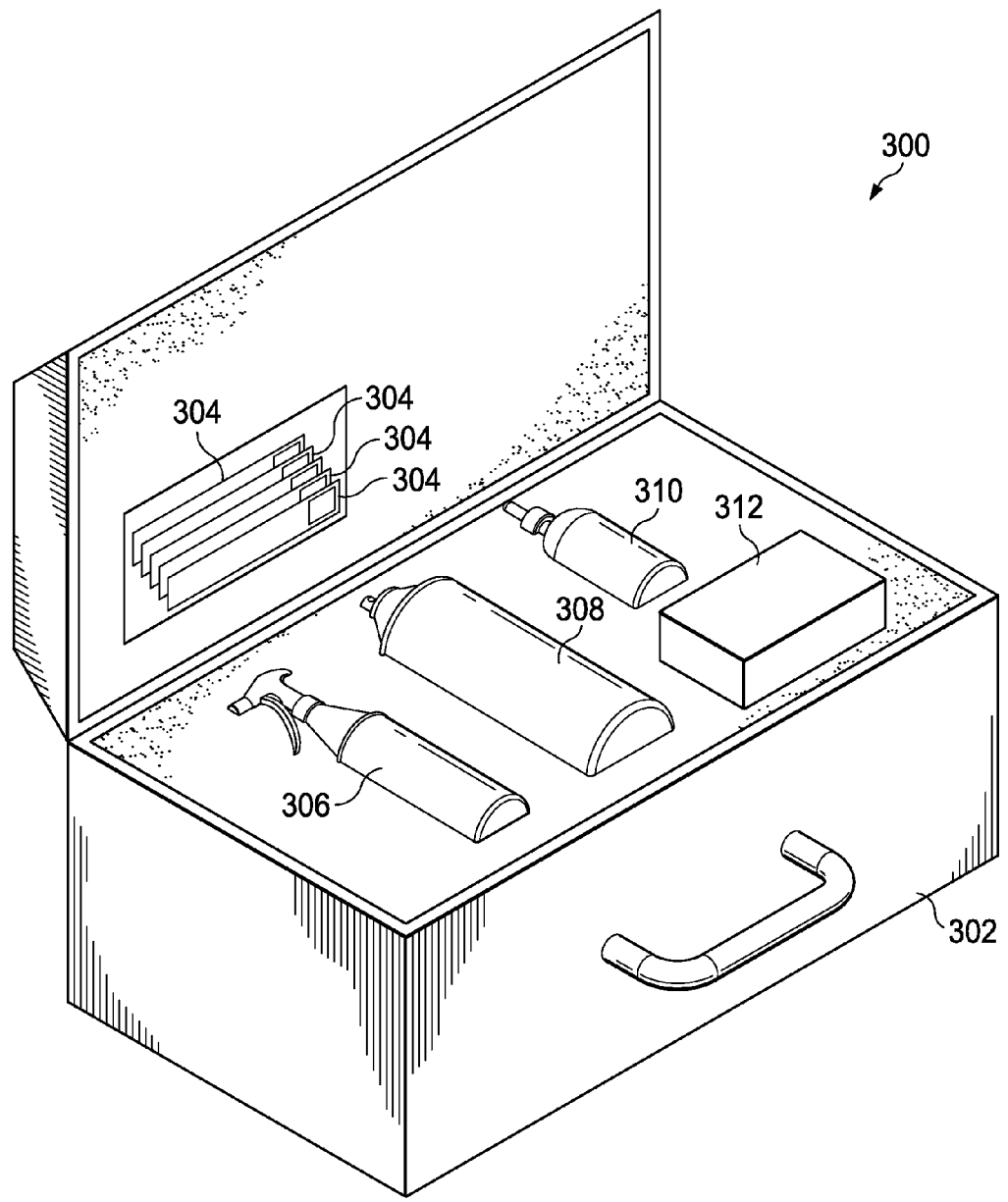
FIG. 3 is an isometric view of a test kit for explosives according to the present disclosure.

Referring now to FIG. 3, an exemplary test kit is shown. The kit 300 may be portable and rugged for use in adverse locations and conditions and the various components may be individually replaceable as they are exhausted. In the present embodiment, a rugged container 302 provides for storage and transportation of the kit 300. The container 302 may be plastic or metallic and may provide for shock resistant packaging as well as locking mechanisms to prevent tampering. Within the container 302 may be a supply of test strips 304 treated with the inks as described above. One or more of an aerosol spray 306, a pump spray 308, and a dropper bottle 310 may also be provided, each of these containing a supply of the testing ink. Various miscellaneous but helpful other items 312 may also be included. A non-limiting example of these items 312 include plastic bags, swabs, patches, capillary tubes, and protective masks, goggles, and gloves.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A method of manufacturing an explosive testing agent comprising:
   synthesizing hydrogen bronze nanoparticles in an aqueous suspension by exposing molybdenum trioxide to an acid salt of a 2-hydroxycarboxylic acid; and
   placing the nanoparticles on a test platform.

2. The method of claim 1 wherein the metal salt of a 2-hydroxycarboxylic acid is sodium gluconate.

3. The method of claim 1, wherein the test platform is a test strip.

4. The method of claim 1, wherein the test platform is a spray device.

5. The method of claim 1, further comprising placing the nanoparticles on a test platform with a wetting agent.

\* \* \* \* \*